United States Patent [19]

Nishiyama et al.

[11] 4,288,599
[45] Sep. 8, 1981

[54] PROCESS FOR PRODUCING PYRIDINE DERIVATIVES HAVING A TRIFLUOROMETHYL GROUP AT β-POSITION THEREOF

[75] Inventors: Ryuzo Nishiyama, Takatsuki; Kanichi Fujikawa, Moriyama; Isao Yokomichi, Moriyama; Yasuhiro Tsujii, Moriyama; Shigeyuki Nishimura, Shiga, all of Japan

[73] Assignee: Ishihara Sangyo Kaisha Ltd., Osaka, Japan

[21] Appl. No.: 124,757

[22] Filed: Feb. 26, 1980

[30] Foreign Application Priority Data

Mar. 9, 1979 [JP] Japan ................................. 54/27369
Apr. 12, 1979 [JP] Japan ................................. 54/44733
Oct. 22, 1979 [JP] Japan ............................... 54/136057

[51] Int. Cl.$^3$ ........................................... C07D 213/26
[52] U.S. Cl. .................................... 546/345; 546/346
[58] Field of Search ............................... 546/345, 346

[56] References Cited

FOREIGN PATENT DOCUMENTS 483 2/1979 European Pat. Off. ............ 546/302
7900094 3/1979 PCT Int'l Appl. ................. 546/302

Primary Examiner—Alan L. Rotman
Attorney, Agent, or Firm—Oblon, Fisher, Spivak, McClelland & Maier

[57] ABSTRACT

Pyridine derivatives having a trifluoromethyl group at β-position thereof are produced by reacting β-picoline with chlorine and hydrogen fluoride in a vapor phase at high temperature for a short time. The reaction condition can be mild and the yield of the object compound is increased by reacting them in the presence of a specific metal fluodie. The pyridine derivatives useful as starting materials for agricultural chemicals and medicines can be continuously obtained by a simple reaction at high yield.

17 Claims, No Drawings

PROCESS FOR PRODUCING PYRIDINE DERIVATIVES HAVING A TRIFLUOROMETHYL GROUP AT β-POSITION THEREOF

BACKGROUND OF THE INVENTION

1. Field of the Invention

The present invention relates to a process for producing a pyridine derivative having a trifluoromethyl group at β-position thereof directly from β-picoline. More particularly, it relates to a process for producing a pyridine derivative having a trifluoromethyl group at β-position thereof by a vapor phase reaction of β-picoline with chlorine and hydrogen fluoride, if necessary, in the presence of a catalyst of a specific metal fluoride.

2. Description of the Prior Arts

Pyridine derivatives having a trifluoromethyl group at β-position thereof have been found to be converted into the important compounds having excellent physiological activities and have been considered as important intermediates for agricultural chemicals and medicines. 2-Chloro-5-trifluoromethylpyridine is especially the important intermediate for herbicides, insecticides and fungicides. Therefore, it has been required to find an industrial process for producing such compounds in a mass production and an economical manner.

Thus, it has not been found so many reports for productions of said pyridine derivatives since the utilities of said pyridine derivatives have not been considered to be important.

It has been described that a chlorination of methyl group of β-picoline is difficult in a production of β-trichloromethylpyridine which has the similar structure to said pyridine derivatives in HELVETICA CHIMICA ACTA vol. 59, Fase 1, Nr. 19-20, 1976, etc. Therefore, it has not been expected to produce said pyridine derivatives from β-picoline.

Recently, it has been proposed to produce said pyridine derivatives in European Pat. Nos. 0000483 and WO79/00094 etc. In these prior arts, only experimental small scale processes are disclosed. For example, in WO 79/00094, it has been disclosed as a process for producing chloro β-trifluoromethylpyridines, that (1) chlorine gas is fed into a solution of β-picoline in carbon tetrachloride under ultraviolet radiation at 80° C. for 3 hours to produce chloro β-trichloromethylpyridines at an yield of less than 10%; (2) chloro β-trifluoromethylpyridines are produced by reacting the chloro β-trichloromethylpyridines with antimony trifluoride in a liquid phase at 140° to 145° C. for 1 hour or reacting the chloro β-trichloromethylpyridines with hydrogen fluoride in a liquid phase at 200° C. for 10 hours in an autoclave.

The process, however, has the following disadvantages.

(1) it takes a long time for the chlorination and the fluorination;

(2) the chlorination is not smoothly performed to produce a large amount of by-products and to be lower yield and the operations for the purification and the separation are complicated;

(3) anitmony trifluoride is expensive and causes a trouble in a treatment of a waste solution and an autoclave is required for the reaction with hydrogen fluoride.

SUMMARY OF THE INVENTION

The present invention has been attained by the finding that the pyridine derivatives having a trifluoromethyl group at β-position thereof can be obtained by a single step by a vapor phase reaction of β-picoline with chlorine and hydrogen fluoride. The present invention has been also attained by the finding that a reaction velocity is increased in the presence of a specific metal fluoride in said reaction whereby reaction conditions can be mild to easily produce said pyridine derivatives and to remarkably increase the yield.

A first object of the present invention is to provide a process for producing said pyridine derivatives which are important starting materials for agricultural chemicals and medicines with industrial advantages.

A second object of the present invention is to produce directly said pyridine derivatives by a single step from β-picoline.

A third object of the present invention is to provide a process for continuously producing said pyridine derivatives for a short time by a reaction of β-picoline with chlorine and hydrogen fluoride in a vapor phase.

The other objects of the present invention will be clear by the following description.

The foregoing and other objects of the present invention have been attained by providing a process for producing pyridine derivatives having a trifluoromethyl group at β-position thereof and having the formula

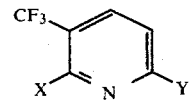

wherein X and Y respectively represent hydrogen atom or chlorine atom which comprises reacting β-picoline with chlorine and hydrogen fluoride by a vapor phase reaction in the presence or the absence of a catalyst of a fluoride of at least one metal selected from the group consisting of aluminum, chromium, iron, nickel, cobalt and manganese.

DETAILED DESCRIPTION OF THE PREFERRED EMBODIMENTS

The diluent can be organic solvents such as halohydrocarbons such as carbon tetrachloride, chloroform, methylene chloride and F-112 ($CFCl_2.CFCl_2$) or F-113 ($CF_2Cl.CFCl_2$) and inert gases such as nitrogen, argon or helium. The diluent has the functions for controlling a combustion, a carbonization, a formation of tar by-products and for sinking heat.

In the process of the present invention, supplies of the starting materials and if necessary, the diluent are carried out as those of the conventional vapor phase reaction. For example, β-picoline, chlorine, hydrogen fluoride and the diluent can be separately fed or a mixture of β-picoline and the diluent and a mixture of chlorine and hydrogen fluoride can be separately fed or they can be fed simultaneously, sequentially or at once or separately.

Amounts of chlorine and hydrogen fluoride are not critical and are depending upon an amount of β-picoline as the starting material, a formation of pyridine derivatives and a kind of the reactor and are respectively in ranges of 2 to 15 moles preferably 2.5 to 10 moles and 2 to 60 moles preferably 2.5 to 10 moles based on 1 mole of β-picoline. An amount of the diluent is usually in a range of 3 to 70 mole based on 1 mole of β-picoline. The reaction temperature is usually in a range of 300° to 600° C. preferably 350° to 500° C. and the residence time of the reaction mixture in the reaction zone is usually in a range of 0.5 to 50 seconds preferably 1 to 30 seconds.

When the specific metal fluoride is incorporated as the catalyst, the reaction velocity is increased whereby reaction conditions can be mild and an yield of the object product is remarkably increased. The object product can be produced by the reaction in the absence of the catalyst, however, the reaction velocity is relatively slow. In the latter, if the reaction velocity is increased, abnormal reactions such as side reactions, decompositions and carbonizations are easily caused. On the other hand, the reaction in the presence of the catalyst can be performed in mild reaction conditions such as a reaction temperature, amounts of chlorine and hydrogen fluoride and a residence time to obtain the object product at high yield. Therefore, the reaction in the presence of the catalyst is remarkably advantageous in an industrial process.

The fluorides of aluminum, chromium, iron, nickel, cobalt or manganese used as the catalyst can be exemplified as follows: for example, chromium(II) fluroide ($CrF_2$), chromium(III) fluoride ($CrF_3$), chromium(IV) fluoride ($CrF_4$) as chromium fluorides; iron(II) fluoride ($FeF_2$), iron(III) fluoride ($FeF_3$) as iron fluorides; nickel(II) fluoride ($NiF_2$), nickel(III) fluoride ($NiF_3$) as nickel fluorides; manganese(II) fluoride ($MnF_2$), manganese(III) fluoride ($MnF_3$), manganese(IV) fluoride ($MnF_4$) as manganese fluorides; cobalt(II) fluodie ($CoF_2$), cobalt(III) fluoride ($CoF_3$) as cobalt fluorides; aluminum(III) fluoride ($AlF_3$) as aluminum fluorides etc.

One or more of the fluorides can be used. Among the catalytic components, a fluoride of chromium, iron or aluminum is preferably used for an industrial purpose.

In usual, such catalytic component is admixed with a carrier such as activated carbon, activated alumina and aluminum(III) fluoride and the mixture is treated in a form of granules or pellets having a desired size and is fed into the reaction zone. the catalytic component in a form of the specific metal fluoride can be fed into the reactor so as to place it in the reaction zone. It is also possible to feed a precursor of the catalyst in a form of the metal or alloy or the metal oxide, chloride, hydroxide or carbonate or a hydrate thereof, into the reactor and then, to feed hydrogen fluoride gas to react them to form the desired fluoride so as to place it in the reaction zone. For example, a carrier of alumina or aluminum-(III) fluoride supporting said precursor such as the specific metal oxide or chloride such as ferric chloride and chromous trioxide is fed into the reactor and hydrogen fluoride is fed at a reaction temperature of 200° to 500° C. to convert the specific metal compound into the specific metal fluoride before the main reaction.

The process of the present invention can be carried out by any reaction system, however, it is practically preferable to perform the reaction in the presence of a fixed bed or a fluidized bed of the solid catalyst in the reaction zone. It is optimum to perform the reaction by fluidizing a suspension of the solid catalyst in a mixed gas containing the starting materials of $\beta$-picoline, chlorine and hydrogen fluoride, the reaction product, hydrogen chloride and the diluent. An amount of the catalytic component is not critical and is usually at a molar ratio of 0.001 to 3 based on $\beta$-picoline.

In the process of the present invention, the chlorination and the fluorination are sequentially and simultaneously performed. As the reaction in view of the starting materials and the product, the reaction for converting a methyl group of $\beta$-picoline into a trifluoromethyl group is mainly found or the reaction for converting a methyl group of $\beta$-picoline into trifluoromethyl group together with selectively introducing chlorine atom at $\alpha$-position (2- and/or 6-position) of the pyridine ring is mainly found. When a chlorine atom is introduced at the $\alpha$-position of the pyridine ring, it is easy to introduce a chlorine atom at 6-position in comparison with 2-position.

The reaction mixture obtained by the above-mentioned reaction contains various intermediates which are not yet converted into the object products together with the object pyridine derivatives.

On the other hand, certain side-reactions to introduce chlorine atoms at $\beta$-, $\gamma$-position or $\alpha$- and $\beta$-positions of the pyridine ring may be performed a little beside the main reaction.

In the process of the present invention, reaction conditions suitable for the kind of the object pyridine derivative are selected from the ranges of the above-mentioned reaction conditions so as to obtain effectively a specific object pyridine derivative. For example, when 2-chloro-5-(and 3-)trifluoromethylpyridine is produced, it is preferable to use chlorine and hydrogen fluoride at molar ratios of 3.5 to 7 and 3 to 10 based on $\beta$-picoline respectively and reacting them at a reaction temperature of 350° to 450° C. for a residence time of 1 to 20 seconds. As a result, the reaction mixture contains 40 to 60 wt.% of 2-chloro-5-trifluoromethylpyridine, 5 to 20 wt.% of 2-chloro-3-trifluoromethylpyridine, 10 to 50 wt.% of 2,6-dichloro-3-trifluoromethylpyridine, 5 to 35 wt.% of $\beta$-trifluoromethylpyridine and 5 to 15 wt.% of other compounds such as $\beta$-chlorodifluoromethylpyridine, 2,5-dichloro-3-trifluoromethylpyridine, 2-chloro-5-chlorodifluoromethylpyridine and 2,3-dichloro-5-trifluoromethylpyridine.

When 2,6-dichloro-3-trifluoromethylpyridine is produced, the reaction is preferably performed in severe reaction conditions of higher ratio of chlorine, higher reaction temperature or longer residence time in comparison with those of the product of 2-chloro-5-(and 3-)trifluoromethylpyridine.

When $\beta$-trifluoromethylpyridine is produced, the reaction is preferably performed in mild reaction conditions of lower ratio of chlorine, lower reaction temperature or shorter residence time in comparison with those of the product of 2-chloro-5-(and 3-)trifluoromethylpyridines.

Among the pyridine derivatives, mono- or di-chlorotrifluoromethylpyridine especially 2-chloro-5-trifluoromethylpyridine are useful as the intermediates for agricultural chemicals. The process of the present invention is especially effective for said production of such pyridine derivatives.

In the specification, the chloro $\beta$-trifluoromethylpyridines means mono- and/or di-chloro $\beta$-trifluoromethylpyridines and the chloro $\beta$-perchlorofluoromethylpyridines means mono- and/or di-chloro $\beta$-perchlorofluoromethylpyridines.

In usual, gaseous materials containing the fluorinated products such as the pyridine derivatives as the main products and the unreacted hydrogen fluoride, chlorine, intermediates, hydrogen chloride as a by-product and the diluent are discharged from the reactor. The pyridine derivatives are separated as a liquid mixture through a desired cooling and condensing device.

In the separation, it is possible to liquefy the object pyridine derivatives, the intermediates, hydrogen fluoride and a part of hydrogen chloride by cooling the gaseous reaction mixture and to treat the separated liquid phase by adding water. The liquid mixture usually contains β-trifluoromethylpyridine, 2-chloro-5-trifluoromethylpyridine, 2-chloro-3-trifluoromethylpyridine, and 2,6-dichloro-3-trifluoromethylpyridine. For example, the pyridine derivatives can be obtained at the yield of higher than 80%. When intermediates such as the chloro β-perchlorofluoromethylpyridines which are not converted into the pyridine derivatives are remained in the liquid mixture, the intermediates can be recycled to the reaction zone after separating and recovering them with the unreacted material or the diluent. The resulting pyridine derivatives can be purified by the conventional purifying treatment such as an extraction, a distillation or a crystallization whereby a single compound of the pyridine derivatives such as 2-chloro-5-trifluoromethylpyridine having high purity can be obtained.

When 2-chloro-5-trifluoromethylpyridine is produced at high yield, the following process is advantageous for an industrial purpose. In this process, the reaction conditions are selected so as to increase the yield of 2-chloro-5-trifluoromethylpyridine regardless of productions of 2-chloro-3-trifluoromethylpyridine and 2,6-dichloro-3-trifluoromethylpyridine.

In such reaction conditions, the following liquid mixture can be obtained.

The liquid mixture usually contains 40 to 60% of 2-chloro-5-trifluoromethylpyridine, 5 to 20% of 2-chloro-3-trifluoromethylpyridine, and 5 to 25% of 2,6-dichloro-3-trifluoromethylpyridine.

From the liquid mixture, 2-chloro-5-trifluoromethylpyridine is separated at high yield.

The residue obtained by the separation of 2-chloro-5-trifluoromethylpyridine contains 0 to 3% of 2-chloro-5-trifluoromethylpyridine, 10 to 35% of 2-chloro-3-trifluoromethylpyridine, and 10 to 50% of 2,6-dichloro-3-trifluoromethylpyridine.

When the residue is hydrogenated, chlorine atom on the pyridine ring is easily substituted by hydrogen atom to produce β-trifluoromethylpyridine. In the hydrogenation, for example, a catalytic reaction of the chloro β-trifluoromethylpyridine with hydrogen in the presence of the specific catalyst was performed. The catalysts can be platinum, palladium, nickel, copper or silver type catalyst.

The reaction can be carried out in a liquid phase or a vapor phase. For example, water, alcohols, ethers, aromatic hydrocarbons can be used in the liquid phase reaction. The reaction temperature is usually in a range of 50° to 200° C. in the liquid phase reaction and in a range of 150° to 400° C. in the vapor phase reaction. In the reaction, trifluoromethyl group of the chloro β-trifluoromethylpyridines is not disconnected, however only chlorine atom is selectively substituted by hydrogen atom whereby β-trifluoromethylpyridine can be produced at high yield. Therefore, β-trifluoromethylpyridine having high purity can be produced at high yield by applying the conventional purifying treatment such as a filtration, an extraction or a distillation. The β-trifluoromethylpyridine is recycled to the step of producting the chloro β-trifluoromethylpyridines so as to reuse it. The β-trifluoromethylpyridine can be easily converted into the chloro β-trifluoromethylpyridines by feeding the β-trifluoromethylpyridine with β-picoline as a mixture or separately. The intermediates which are not converted into the chloro β-trifluoromethylpyridines in the chlorination and fluorination of β-picoline, can be also converted into the chloro β-trifluoromethylpyridines by treating the intermediates in the hydrogenation and then recycling them to the step of producing the chloro β-trifluoromethylpyridines.

The present invention will be further illustrated by certain examples, however it is not limited by the description of the examples.

EXAMPLE 1

A stainless steel reaction tube having an inner diameter of 42 mm and a length of 1250 mm as a reaction zone was used. A stainless steel preheating tube having an inner diameter of 20 mm and a length of 500 mm was used for a preheating of hydrogen fluoride and chlorine. A stainless steel preheating tube having an inner diameter of 30 mm and a length of 500 mm was used for a preheating of β-picoline and carbon tetrachloride.

The reaction tube and the preheating tubes were covered by each electric heater and each insulator so as to control the temperature outwardly and they were respectively placed in slant positions.

Into the reaction tube, 47 g. (0.5 mole) of β-picoline and 770 g. (5 mole) of carbon tetrachloride which were preheated to 230° C. and 181 g. (2.55 mole) of chlorine and 520 g. (26 mole) of hydrogen fluoride which were preheated to 300° C. were respectively fed during about 100 minutes at substantially constant flow rate to carry out a vapor phase reaction at 430° C. A residence time of the reaction mixture in the reaction zone was about 5 seconds.

The gas discharged from the reaction tube was condensed by passing it through a water scrubbing column and a caustic alkali scrubbing column. The resulting oily product was separated and washed with water and dehydrated over sodium sulfate and then, carbon tetrachloride was distilled off under a reduced pressure to obtain 77 g. of an oily product. The oily product was analyzed by a gas chromatography with a temperature programmer. In the recovered organic materials, the chloro β-trifluoromethylpyridines were obtained at a ratio of 60.5 wt.% and the intermediates such as the chloro β-perchlorofluoromethylpyridines were obtained at a ratio of about 40 wt.%. The result of the analysis of the oily product by the gas chromatography is shown in the following table 1.

EXAMPLE 2

In the reaction tube used in Example 1, 28 g. (0.3 mole) of β-picoline and 277 g. (1.8 mole) of carbon tetrachloride which were preheated to 250° C. and 149 g. (2.1 mole) of chlorine and 30 g. (1.5 mole) of hydrogen fluoride which were preheated to 300° C. were fed during 30 minutes. The vapor phase reaction was carried out at a reaction temperature of 410° C. and a residence time of the reaction mixture of 9.5 seconds.

The gas discharged from the reaction tube was treated as the process of Example 1 to obtain 44 g. of an oily product. The result of the analysis of the oily product by the gas chromatography is shown in the following table 1.

The data of the other components in the table show a percent of a total of compounds such as the chloro β-perchlorofluoromethylpyridines.

TABLE 1

| | Exp. 1 | Exp. 2 |
|---|---|---|
| 2-chloro-5-trifluoromethyl- | | |

TABLE 1-continued

|  | Exp. 1 | Exp. 2 |
| --- | --- | --- |
| pyridine (%) | 33.2 | 36.4 |
| 2-chloro-3-trifluoromethyl-pyridine (%) | 10.7 | 8.7 |
| 2,6-dichloro-3-trifluoro-methylpyridine (%) | 16.6 | 12.8 |
| Other components (%) | 39.5 | 42.1 |

EXAMPLE 3

A stainless steel reaction tube having an inner diameter of 42 mm and a length of 1250 mm was used as a reaction zone. A catalyst layer having a length of 250 mm was formed at a distance of 500 mm from the inlet of the reaction tube. A stainless steel preheating tube having an inner diameter of 20 mm and a length of 500 mm was used for a preheating of anhydrous hydrogen fluoride and chlorine. A stainless steel preheating tube having an inner diameter of 20 mm and a length of 500 mm was used for a preheating of β-picoline and carbon tetrachloride. The reaction tube and the preheating tubes were covered by each electric heater and each insulator so as to control the temperature outwardly, and they were respectively placed in slant positions.

In the catalyst packing part of the reaction tube, a mixture of 0.03 mole of chromium(III) fluoride hydrate and 200 g. of active alumina having a particle size of 4 to 6 mm was packed and the reaction tube was heated to 430° C. and anhydrous hydrogen fluoride was fed at a rate of 1 g./min. for 2 hours to activate it. Then, 280 g. (3 mole) of β-picoline and 2310 g. (15 mole) of carbon tetrachloride which were preheated to 230° C. and 960 g. (13.5 mole) of chlorine and 480 g. (24 mole) of anhydrous hydrogen fluoride which were preheated to 300° C. were fed during 290 minutes at the substantially same rates into the reaction tube to carry out a vapor phase reaction at 430° C. to react them. The residence time of the reaction mixture in the reaction zone was about 9 seconds.

The gas discharged from the reaction tube was condensed by passing it through a water scrubbing column and a caustic alkali scrubbing column. The oily product was separated and washed with water and dehydrated over sodium sulfate and then, carbon tetrachloride was distilled off under a reduced pressure to obtain 420 g. of an oily product. The oily product was analyzed by a gas chromatography with a temperature programmer. The result is shown in the following table 2.

EXAMPLE 4

In the catalyst packing part in the reaction tube used in Example 3, 300 g. of γ-alumina was fed and was activated by the hydrogen fluoride. Then, 465 g. (5 mole) of β-picoline and 3850 g. (25 mole) of carbon tetrachloride which were preheated to 250° C. and 1950 g. (27.5 mole) of chlorine and 900 g. (45 mole) of hydrogen fluoride which were preheated to 300° C. were respectively fed during about 8 hours at substantially same rates. The vapor phase reaction was carried out at a reaction temperature of 430° C. and a residence time of the reaction mixture in the reaction zone was 10.5 seconds.

In accordance with the process of Example 3, the gas discharged from the reaction tube was treated to obtain 708 g. of an oily product.

The result of the analysis of the oily product by the gas chromatography is shown in the following table 2.

EXAMPLE 5

In accordance with the process of Example 4 except using a catalyst supporting 0.1 mole of nickel(II) fluoride hydrate on 200 g. of active carbon having a particle size of 2 to 4 mm., the catalyst was used instead of 300 g. of γ-alumina and the catalytic activation of alumina by anhydrous hydrogen fluoride, the vapor phase reaction was carried out to obtain 300 g. of an oily product.

The result of the analysis of the oily product by the gas chromatography is shown in the following table 2.

The data of the other components in the table show a percent of a total of compounds such as the chloro β-perchlorofluoromethylpyridines.

TABLE 2

|  | Exp. 3 | Exp. 4 | Exp. 5 |
| --- | --- | --- | --- |
| 2-chloro-5-trifluoromethyl-pyridine (%) | 54.8 | 51.8 | 48.6 |
| 2-chloro-3-trifluoromethyl-pyridine (%) | 13.8 | 18.2 | 17.9 |
| 2,6-dichloro-3-trifluoro-methylpyridine (%) | 17.5 | 22.6 | 23.4 |
| Other components (%) | 13.9 | 7.4 | 10.1 |

EXAMPLE 6

A vertical reaction tube made of Inconel having a reaction zone of a catalyst fluidized bed (an inner diameter of 82 mm and a height of 1100 mm) was used as a reactor. Two preheating tubes made of Inconel having an inner diameter of 8 mm and a length of 2000 mm for the starting material and the diluent were connected to the reaction tube. The reaction tube and the preheating tubes were covered by each electric heater and each insulator so as to control the temperature outwardly.

The activated catalyst used in Example 3 was pulverized to give a particle diameter of 0.18 to 0.4 mm. In the reaction zone, 1.7 kg. of the product was charged as the catalyst.

The reactor was heated at 430° C. and β-picoline was fed at a rate of 3.6 g./min. and nitrogen gas was fed at a rate of 11.3 l/min. through the preheating tube and chlorine gas was fed at a rate of 2.8 l/min. and anhydrous hydrogen fluoride was fed at a rate of 2.5 l/min. through the other preheating tube. They were respectively fed into the reaction tube as the mixed gases at about 200° C. to react them for about 5 hours. The residence time of the reaction mixture in the reaction zone was about 7 seconds.

The gas discharged from the reactor was treated as the process set forth in Example 3 to obtain 1680 g. of an oily product.

The result of the analysis of the oily product by the gas chromatography with a temperature programmer is shown in the table 3.

EXAMPLE 7

In accordance with the process of Example 6 except that β-picoline was fed at a rate of 2.38 g./min.; 3-trifluoromethylpyridine was fed at a rate of 1.88 g./min. and nitrogen gas was fed at a rate of 11.3 l/min. and also chlorine gas was fed at a rate of 2.8 l/min. and anhydrous hydrogen fluoride was fed at a rate of 2.5 l/min. to react them for about 3 hours, the reaction was carried out. The residence time of the reaction mixture in the reaction zone was about 7 seconds.

The gas discharged from the reactor was treated by the process as set forth in Example 3 to obtain 1090 g. of an oily product.

The result of the analysis of the oily product by the gas chromatography is shown in table 3.

The data of the other components in the table show a percent of a total of compounds such as the chloro β-perchlorofluoromethylpyridines.

TABLE 3

|  | Exp. 6 | Exp. 7 |
|---|---|---|
| 2-chloro-5-trifluoromethyl-pyridine (%) | 51.5 | 56.4 |
| 2-chloro-3-trifluoromethyl-pyridine (%) | 6.6 | 9.6 |
| 2,6-dichloro-3-trifluoro-methylpyridine (%) | 25.1 | 18.3 |
| Other components (%) | 16.8 | 15.7 |

EXAMPLE 8

(1) Production of chloro β-trifluoromethylpyridines

A vertical reaction tube made of Inconel having a reaction zone of a catalyst fluidized bed (an inner diameter of 151 mm and a height of 1440 mm) was used as a reactor. Two preheating tubes made of Inconel having an inner diameter of 40 mm and a length of 1500 mm for the starting materials and the diluent were connected to the reaction tube. The reaction tube and the preheating tubes were covered by each electric heater and each insulator so as to control the temperature outwardly.

A mixture of 970 g. of chromium(III) fluoride hydrate and 12 kg. of active alumina having a particle size of 0.18 to 0.4 mm was charged into the catalyst packing part. The reaction tube was heated at 430° C. and hydrous hydrogen fluoride was fed at a rate of 20 l/min. for 3 hours to activate it.

The reactor was heated at 430° C. and β-picoline was fed at a rate of 17 g./min, nitrogen gas was fed at a rate of 41 l/min. through the preheating tube and chlorine gas was fed at a rate of 21 l/min. and anhydrous hydrogen fluoride was fed at a rate of 21 l/min. through the other preheating tube. They were respectively fed into the reaction tube as the mixed gases at about 200° C. to react them for about 100 hours. The activated catalyst was continuously fed and discharged at a rate of 3 kg./hour during the reaction. The residence time of the reaction mixture in the reaction zone was about 2.5 seconds.

The gas discharged from the reactor was passed through a water scrubbing colum and a caustic alkali scrubbing column. The oily product was separated and washed with water to obtain 160 kg. of the oily mixture of chloro β-trifluoromethylpyridines. The oily product was purified to obtain 72 kg. of 2-chloro-5-trifluoromethylpyridine. After separating by-products with a distillation, 72 kg. of the mixture of chloro β-trifluoromethylpyridines containing 2.6% of 2-chloro-5-trifluoromethylpyridine, 13% of 2-chloro-3-trifluoromethylpyridine and 50% of 2,6-dichloro-3-trifluoromethylpyridine was obtained as the residue obtained by the separation of the object compound.

(2) Production of β-trifluoromethylpyridine

In a 100 liter autoclave, 13.5 kg. of the mixture of the chloro β-trifluoromethylpyridines, 14 kg. of triethylamine, 15 liters of water and 65 g. of 2% palladium on carbon were charged. Hydrogen gas was introduced into the autoclave. The catalytic reduction was carried out at a reaction temperature of 75° C. for 120 minutes under a hydrogen pressure of 20 kg./cm². After the reaction, the catalyst was separated by a filtration and a small amount of dilute hydrochloric acid was added to the filtrate to adjust pH to 3.5. The oil phase was separated and distilled to obtain 8.4 kg. of an oily product (β-trifluoromethylpyridine:β-difluoromethylpyridine=9:1). A small amount of a dilute aqueous solution of sodium hydroxide was added to be an alkaline condition and 12.3 kg. of triethylamine was recovered.

(3) Production of chloro β-trifluoromethylpyridines

In accordance with the former step of producing the chloro β-trifluoromethylpyridines except that β-picoline was fed at a rate of 11.3 g./min.; the hydrogenated product was fed at a rate of 8.9 g./min.; nitrogen gas was fed at a rate of 41 l/min.; and also chlorine gas was fed at a rate of 21 l/min. and anhydrous hydrogen fluoride was fed at a rate of 21 l/min. to react them for about 3 hours, the reaction was carried out. The residence time of the reaction mixture in the reaction zone was about 2.5 seconds.

In accordance with the former step of producing the chloro β-trifluoromethylpyridines, the gas discharged from the reactor was treated to obtain 44 kg. of the oily mixture of chloro-β-trifluoromethylpyridines.

The product was analyzed by a gas chromatography with a temperature programer to find that the product contained 58.5% of 2-chloro-5-trifluoromethylpyridine, 11.4% of 2-chloro-3-trifluoromethylpyridine, 16.2% of 2,6-dichloro-3-trifluoromethylpyridine and 13.9% of the other components such as β-trifluoromethylpyridine, 2,5-dichloro-3-trifluoromethylpyridine, 2,3-dichloro-5-trifluoromethylpyridine, chloro β-chlorodifluoromethylpyridines. The product was distilled to obtain 21.9 kg. of the object 2-chloro-5-trifluoromethylpyridine.

EXAMPLE 9

A vertical reaction tube made of Inconel having a catalyst fluidized bed (an inner diameter of 97.1 mm and a height of 1570 mm) was used as a reactor. Two preheating tubes made of Inconel having an inner diameter of 30 mm and a length of 1,000 mm for the starting materials and the diluent were connected to the reaction tube. The reaction tube and the preheating tubes were covered by each electric heater and each insulator so as to control the temperature outwardly.

A mixture of 277 g. of anhydrous ferric chloride and 2.2 kg. of aluminum(III) fluoride having a particle size of 105μ~250μ was charged into the catalyst packing part. The reaction tube was heated at 200° C. and anhydrous hydrogen fluoride was fed at a rate of 2.3 l/min. for 1 hour to activate it.

The reactor was heated at 400° C. and β-picoline was fed at a rate of 6.8 g./min., nitrogen gas was fed at a rate of 9.9 l/min. through the preheating tube. Chlorine gas was fed at a rate of 7.4 l/min. and anhydrous hydrogen fluoride was fed at a rate of 7.4 l/min. through the other preheating tube. They were respectively fed into the reaction tube as the mixed gases at about 200° C. to react them for about 30 hours. The activated catalyst was continuously fed and discharged at a rate of 300 g./hour during the reaction. The residence time of the reaction mixture in the reaction zone was about 3.4 seconds.

The gas discharged from the reactor was passed through a water scrubbing column and a caustic alkali scrubbing column. The condensed product was separated and neutralized by an ammonia solution to obtain 19.11 kg. of an oily product by a steam distillation. Further, the oily product was distilled to obtain 1.53 kg. of a forerun containing β-trifluoromethylpyridine as a main component, 9.56 kg. of a main distillate containing 2-chloro-5-trifluoromethylpyridine and 7.62 kg. of a last distillate containing 3.7% of 2-chloro-5-trifluoromethylpyridine, 14.5% of 2-chloro-3-trifluoromethylpyridine, 47.7% of 2,6-dichloro-3-trifluoromethylpyridine and 34.1% of other components.

EXAMPLE 10

In accordance with the production step of the chloro β-trifluoromethylpyridines of the Example 8 except that chlorine gas was fed at a rate of 4.9 l/min., and the reaction was performed at a temperature of 380° C., in the residence time of about 3.9 seconds and for 6 hours, the production was carried out.

The gas discharged from the reactor was condensed through a water scrubbing column and a caustic alkali scrubbing column. Further the condensed product was washed with an aqueous caustic alkali solution and water to obtain 8.2 kg. of an oil. This oil was dried and distilled to obtain 5.8 kg. of β-trifluoromethylpyridine.

EXAMPLES 11-12

In accordance with the process of Example 5 except for using respectively a catalyst supporting 0.1 mole of manganese(III) fluoride and a catalyst supporting 0.1 mole of cobalt(II) fluoride, the catalysts were used instead of the catalyst of nickel(II) fluoride, the vapor phase reaction was carried out to obtain respectively 340 g. and 280 g. of an oily product.

The result of the analysis of the oily product by the gas chromatography is shown in the following table 4 which is represented in the same manner as the table 2.

TABLE 4

| Catalyst | Exp. 11 MnF$_3$ | Exp. 12 CoF$_2$ |
|---|---|---|
| 2-chloro-5-trifluoromethyl-pyridine (%) | 39.7 | 32.2 |
| 2-chloro-3-trifluoromethyl-pyridine (%) | 14.8 | 12.3 |
| 2,6-dichloro-3-trifluoromethyl-pyridine (%) | 22.8 | 18.1 |
| Other components (%) | 22.7 | 37.4 |

EXAMPLE 13

In accordance with the Example 10, except for that chlorine gas was fed at a rate of 16.6 l/min., hydrogen fluoride was fed at a rate of 12.9 l/min., β-picoline was fed at a rate of 10.5 g./min. and nitrogen gas was fed at a rate of 25.2 l/min., the reaction was performed at a temperature of 440° C., in the residence time of about 3.7 seconds and for 4.5 hours.

The gas discharged from the reactor was condensed, purified and separated by the same manner as the Example 10 to obtain 3.1 kg. of 2,6-dichloro-3-trifluoromethylpyridine.

We claim:

1. A process for producing a pyridine derivative having a trifluoromethyl group at the β-position thereof and having the formula:

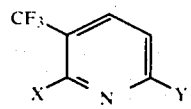

wherein X and Y, respectively, are hydrogen or chloro which comprises reacting β-picoline with chlorine and hydrogen fluoride by a vapor phase reaction in the absence of a catalyst.

2. A process according to claim 1 wherein said reaction is carried out in the presence of a diluent.

3. A process according to claim 1 wherein said reaction is carried out at 300° to 600° C.

4. A process according to claim 1, wherein the residence time of the reaction mixture in the reaction zone is from 0.5 to 50 seconds.

5. A process according to claim 1 wherein said pyridine derivative is 2-chloro-3-trifluoromethylpyridine, 2-chloro-5-trifluoromethylpyridine or 2,6-dichloro-3-trifluoromethylpyridine.

6. A process according to claim 1 wherein said pyridine derivative is 2-chloro-5-trifluoromethylpyridine.

7. A process according to claim 1 wherein said pyridine derivative is β-trifluoromethylpyridine.

8. A process for producing a pyridine derivative having a trifluoromethyl group at the β-position thereof and having the formula:

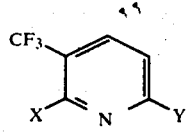

wherein X and Y, respectively, are hydrogen or chloro which comprises reacting β-picoline with chlorine and hydrogen fluoride by a vapor phase reaction in the presence of a catalyst comprising a fluoride of a metal selected from the group consisting of aluminum, chromium, iron, nickel, cobalt, manganese, chromium with aluminum, iron with aluminum, manganese with aluminum, and cobalt with aluminum.

9. A process according to claim 8, wherein said reaction is carried out in the presence of a diluent.

10. A process according to claim 8, wherein said reaction is carried out at 300° to 600° C.

11. A process according to claim 8, wherein the residence time of the reaction mixture in the reaction zone is from 0.5 to 50 seconds.

12. A process according to claim 8, wherein said reaction is carried out in the presence of a catalyst comprising a fluoride of a metal selected from the group consisting of aluminum, chromium, iron, nickel, cobalt and manganese.

13. A process according to claim 8, wherein said pyridine derivative is 2-chloro-3-trifluoromethylpyridine, 2-chloro-5-trifluoromethylpyridine or 2,6-dichloro-3-trifluoromethylpyridine.

14. A process according to claim 8, wherein said pyridine derivative is 2-chloro-5-trifluoromethylpyridine.

15. A process according to claim 8, wherein said pyridine derivative is β-trifluoromethylpyridine.

16. A process according to claim 8, wherein the catalyst is suspended in a gas flow containing the reaction mixture to carry out said reaction in a fluidized condition.

17. A process according to claim 8, wherein said catalyst is a fluoride of aluminum, iron or chromium.

* * * * *